United States Patent [19]
Nosov

[11] Patent Number: 5,481,196
[45] Date of Patent: Jan. 2, 1996

[54] PROCESS AND APPARATUS FOR MICROWAVE DIAGNOSTICS AND THERAPY

[75] Inventor: Eugene Nosov, Omaha, Nebr.

[73] Assignee: Nebraska Electronics, Inc., Omaha, Nebr.

[21] Appl. No.: 336,392

[22] Filed: Nov. 8, 1994

[51] Int. Cl.$^6$ .................................................. G01R 23/16
[52] U.S. Cl. ......................... 324/637; 324/633; 324/76.12; 128/653.1
[58] Field of Search ..................................... 324/630, 633, 324/637, 76.12, 76.13, 76.14, 76.19; 128/653.1, 659; 600/10

[56] References Cited

U.S. PATENT DOCUMENTS 5,417,211  5/1995  Abraham-Fuchs et al. .......... 128/653.1

Primary Examiner—Kenneth A. Wieder
Assistant Examiner—Glenn W. Brown
Attorney, Agent, or Firm—Suiter & Associates

[57] ABSTRACT

A method and device are disclosed for receiving, analyzing, generating and transmitting microwave electomagnetic radiation in the range of 30 to 300 GHz with spectral power density less than $10^{-9}$ W/Hz. Practice of the invention allows analysis of the microwave spectra of living organisms. Aberrations in the spectrum of a target organism may be identified by comparison with a control organism or with a standardized spectrum. A corrective microwave spectrum may then be administered in an accurate and efficient manner under continuous monitoring. The device disclosed is comprised of receiving and transmitting antennas connected to a multi-channel retranslator, a controlled source of microwave spectra, and measuring and controlling systems.

8 Claims, 2 Drawing Sheets

PROCESS AND APPARATUS FOR MICROWAVE DIAGNOSTICS AND THERAPY

TECHNICAL FIELD

This invention relates to the reception, analysis, generation and projection of microwave electromagnetic radiation during the assessment and treatment of living organisms.

BACKGROUND ART

That electromagnetic radiation has played a crucial role in the development of living organisms is axiomatic. Obvious examples of this principle are the mutagenic effects of ionizing radiation and the evolution of photosynthesis and vision. That living organisms generate and transmit electromagnetic waves is a relatively new discovery, the implications of which are currently under investigation. Analysis of organic microwave electromagnetic emissions suggests different cell types within an organism have distinctive steady states, as does the organism as a whole. Adaptive shifts occur in these baseline microwave spectra in response to external and internal variables. Certain disease processes, (e.g., cancer) have been shown to alter cellular oscillation patterns, suggesting the possibility of noninvasive diagnosis by analysis of microwave electromagnetic radiation (MEMR). Moreover, cells with disturbed steady states may be induced to resume their original resonance levels through exposure to timed, focused MEMR of the appropriate wavelength. Specific cellular behavior, such as synchronous cell division, is also inducible by exposure to MEMR of specific frequencies. Such observations suggest the possibility of noninvasive therapeutic applications. With the proliferation of microwave technologies in communications and industrial applications, concerns have been raised about the inadvertent deleterious alteration of cell function through ambient exposure; this also warrants investigation.

The present invention is designed to analyze and replicate the MEMR spectrum of a control organism, then project that organism's MEMR to a target organism while continuously monitoring the biophysical status of the control and target organisms. The intent is to induce the target organism to adopt the electromagnetic oscillation patterns of the control organism. The device may also be used to analyze the MEMR spectrum of a target organism, generate an appropriate MEMR spectrum, treat and continuously monitor a target organism without employing a control organism.

This invention has a degree of similarity to the device described by Sitko et al in U.S. Pat. No 5,152,286 (Oct. 6, 1992), "Method of microwave resonance therapy and device therefor." The method described therein is the application of MEMR in the form of noise signals to specific "biologically active points" (BAPs, or acupressure/acupuncture sites) of humans experiencing physical or affective disorders. The duration of therapy, using noise signals in the range of 1 to 10 mm wavelength, and $10^{-6}$ to $10^{-18}$ W/Hz spectral power density, is specified to be no longer than 30 minutes. One to 15 sessions are prescribed depending on the condition being treated, and the response to treatment.

In the Sitko regime, a broad spectrum of microwave "noise" is delivered to the target organism. The organism is expected to spontaneously select and respond to those elements of the MEMR spectrum with which resonant interaction occurs. While organisms which have sustained minor damage are able to accomplish this selection, organisms with significant derangement of function have lost the ability to do so. Thus, the Sitko protocol is not effective in many applications. Further, the Sitko device which generates the microwave signals has no capacity to receive or analyze biophysical information such as blood pressure, temperature, or other variables from an organism. Using this device, one cannot monitor the efficacy of treatment, nor can one discern the baseline MEMR spectrum of the target organism. These limitations constitute serious shortcomings which blunt the investigational and therapeutic capacities of the described method and device.

Another limitation of the current art is the inability to identify the aberrant elements of a complex MEMR spectrum in a dysfunctional organism in order to diagnose a particular malady or generate and deliver a normalizing MEMR spectrum. In addition to loss of valuable diagnostic information this inability to target the appropriate resonant frequencies leads to longer therapeutic episodes, reduced efficiency, and greater exposure to microwave radiation.

DISCLOSURE OF THE INVENTION

The apparatus consists of receiving, measuring, analyzing, amplifying and transmitting components. The MEMR spectrum generated by a target organism is taken up through receiving antennas and passed through a measurement system which continuously records the MEMR spectrum. This information reaches a control analyzing system which determines the consonance or dissonance of the MEMR spectrum with an established pattern for the organism, or with the MEMR spectrum of a control source (a second organism). The operator then elects to irradiate the target organism either with a particular spectral range, or with the full spectrum MEMR received from the control organism. The chosen MEMR spectrum is generated within the retranslator and delivered to the target organism by transmitting antennas. During therapy selected biophysical features of the target organism are continuously monitored through an information channel. Responsive adjustments in the transmitted spectrum may be made by the operator, or the control analyzing system may be programmed to respond automatically to predetermined changes in the biophysical status. Upon completion of a therapeutic episode the MEMR spectrum of the target organism is again measured. If dissonance remains the apparatus is adjusted to a new spectrum in order to achieve consonance of the MEMR with the desired pattern. When resonance is achieved and maintained for a satisfactory length of time, treatment is complete.

OBJECTS OF THE INVENTION

It is a primary object of the present invention to provide a device capable of receiving, analyzing, generating and transmitting MEMR spectra from and to living organisms.

Another object of the present invention is to provide a device which can transmit MEMR spectra in a predetermined range and density.

Another object of the present invention is to provide a device which can identify and display variances in spectra between two organisms.

Another object of the present invention is to provide a device which can monitor the biophysical status of a target organism while MEMR irradiation of that organism is occurring.

Still another object of the present invention is to provide a device which can receive the MEMR spectrum from one organism and transmit an identical MEMR spectrum, or any portion thereof, to another organism.

Yet another object of the present invention is to provide a device with which microwave radiation therapy can be conducted more effectively, more efficiently and with lower levels of microwave exposure than previously possible.

Further objects and advantages of the instant invention will become apparent from a consideration of the drawings and ensuing descriptions.

DESCRIPTION OF AN EXEMPLARY EMBODIMENT

The MEMR spectrum from the target organism is accumulated through cutaneous attachment of the receiving horn antennas to selected anatomical sites, in a manner analogous to the attachment of ECG leads. Traditionally, acupuncture/ acupressure sites (biologically active points or BAPs) have been employed for signal receipt and transmission; they are selected on the basis of their classical therapeutic associations and anatomical locations. Simultaneously, selected biophysical characteristics such as pulse, blood pressure, blood oxygenation, electrocardiac activity, electroencephalic activity and other parameters are measured and monitored. The choice of biophysical characteristics, like the choice of BAPs, is based on the nature of the disturbance to be treated; this process is apparent to those skilled in the art.

Upon receipt of the target organism's spectrum through the multi-channel translator, the retranslator conducts an assessment of the spectral characteristics of the organism's MEMR. The spectrum generated by the target organism may be compared either to a population-based normalized range, or to an MEMR spectrum generated by a second, control organism. Those elements of the target organism's profile differing from the normal profile and/or the control profile may then be identified.

If a particular spectral element is found to be deficient or deranged, the device is programmed to supply that oscillation pattern within a range of 1 to 10 mm wavelength and less than $10^{-9}$ W/Hz spectral power density. If a discrete deficiency or derangement is not identified, the device is programmed to supply an MEMR profile which duplicates either that of a population-based norm or that of a control organism whose MEMR spectrum is received through the previously mentioned receiving antennas. Selected biophysical characteristics of the target organism are continually monitored during transmission of the MEMR spectrum. The duration of a therapeutic episode, which in no event would exceed 30 minutes, is determined in part on the basis of the biophysical measurements collected during irradiation, and in part on the status of the organism's MEMR at the conclusion of the therapeutic episode.

Figure 1:
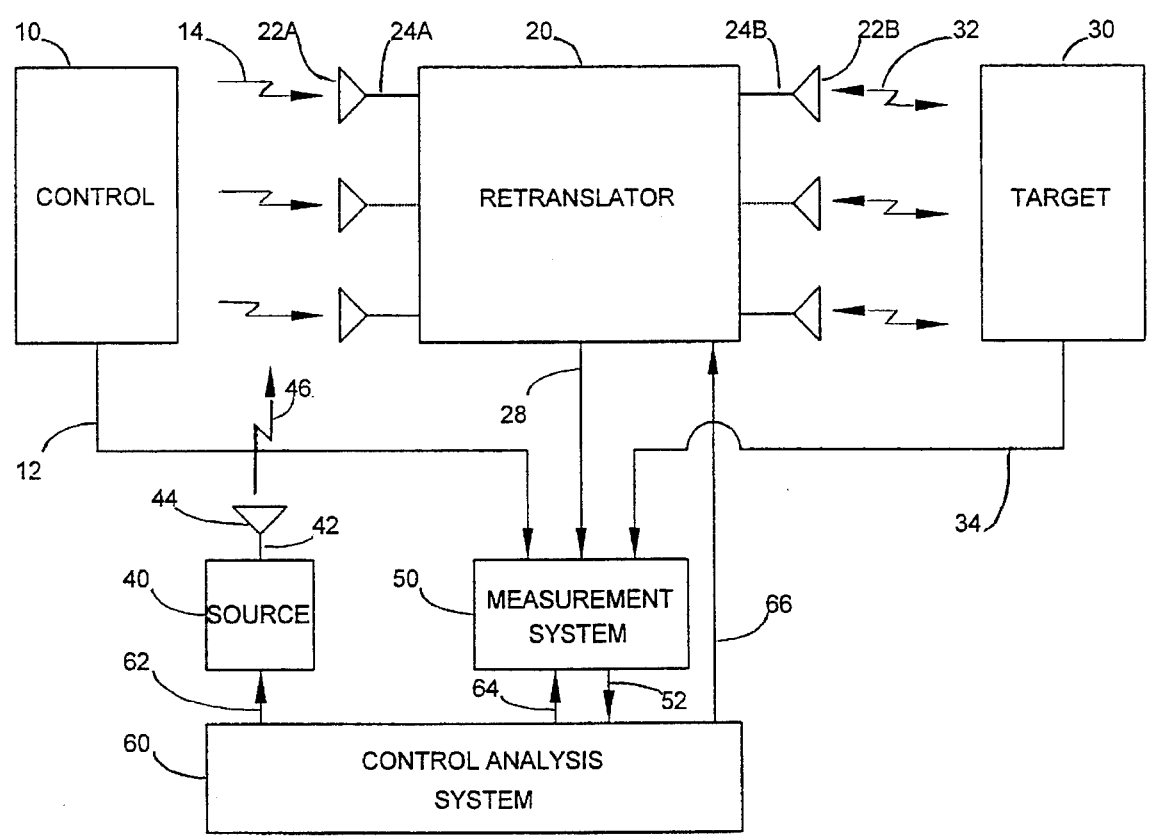
FIG. 1 is a block diagram of the apparatus for microwave diagnostics and therapy showing the internal components and the relationship of the device to a targeted organism as well as to a control organism.

The Apparatus for microwave diagnostics and administration, depicted with a flow diagram in FIG. 1, functions as follows:

The Baseline MEMR (14) of a healthy control organism (10) is received by antennas (22a) attached to biologically active points as described above. Simultaneously, biophysical information is transmitted from the control organism through informational channel (12) and from the target organism through informational channel (34) to the measurement system (50).

Alternatively, an electronically controlled source of MEMR (40) may be employed to generate an MEMR spectrum for a target organism when the organism's selective functions are intact or the therapeutic spectral characteristics are known. In this case the MEMR spectrum (46) is transmitted from the controlled source (40) through a wave guide channel (42) and transmitting antenna (44) to the same receiving antennas (22a) employed for a living control. From these antennas the signals are carried by wave guide channels (24a) to the retranslator (20).

The incoming data from informational channels (12) and (34) and wave guide channel (28) are transmitted to a measurement system (50) where they are subjected to primary processing and analysis. Thereafter, data are transmitted to the controlling-analyzing system (60) through another informational channel (52). The controlled source of MEMR (40), the measurement system (50) and the retranslator (20) are all under the governance of the control analyzing system (60) by way of transmission channels (62), (64) and (66), respectively.

Figure 2:
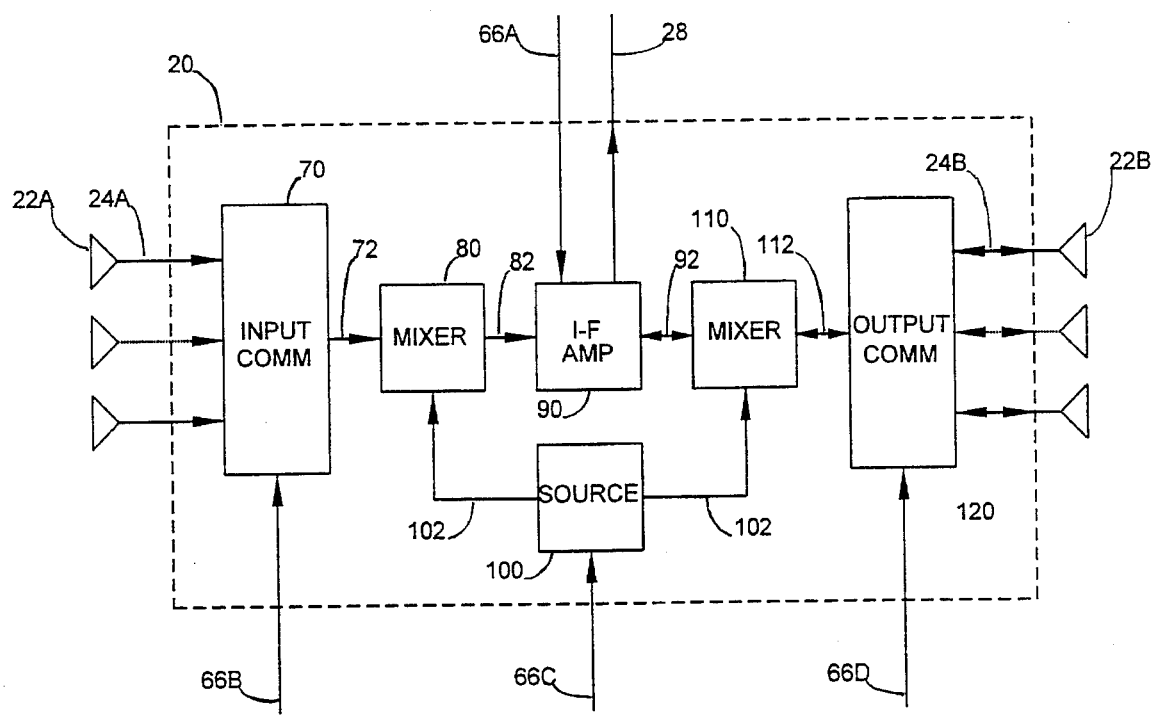
FIG. 2 is a block diagram of the retranslator component of the apparatus showing its internal pathways and functions.

The preferred embodiment of the retranslator is illustrated in FIG. 2. The retranslator consists of a linear sequence as follows:

(a) receiving antennas (22a);

(b) wave guide channels (24a) made of flexible dielectric wave guides;

(c) multi-channel input commutator (70) made with p-i-n diodes;

(d) wave guide channel (72);

(d) mixer (80) maintained at a temperature of no more than 50 K, having a frequency within 30 to 300 GHz, and made upon a cooled Josephson junction;

(e) wave guide channel (82);

(f) intermediate frequency amplifier (90) with noise temperature of no more than 25 K, frequency within 8 to 12 GHz, and made upon a cooled HEMT;

(g) wave guide channel (92);

(h) mixer (110);

(i) wave guide channel (112);

(j) multi-channel output commutator (120), identical to multi-channel input commutator (70);

(k) wave guide channels (24b);

(l) transmitting antennas (22b) to be attached to selected BAPs of the target organism, engineered in the same manner receiving antennas (22a) are linked through wave guide channels (24a) to multi-channel input commutator (70).

Intersecting the foregoing sequence:

(a) a spectrum is transmitted to mixers (80) and (110) from a source of MEMR (100) with controlled frequency through parallel Heterodyne channels (102). The frequency of the Heterodyne (100) is controlled through channel (66c).

(b) multi-channel input and output commutators (70) and (120) are controlled through channels (66b) and (66d), respectively.

(c) control by gain of the intermediate frequency amplifier (90) is accomplished through controlling channel (66a). The signal of the intermediate frequency amplifier is carried to the measurement system (50) through wave guide channel (28).

The retranslating device functions as follows:

The MEMR spectrum received from a control organism's BAPs by antennas (22a) is sent through wave guide channels (24a) to a multi-channel input commutator (70). Though serial connection to mixer (80) and regulation by controlling channel (66b), the incoming MEMR spectrum with frequency band of 30 to 300 GHz is converted to frequency band of 8 to 12 GHz. The signal of the Heterodyne (100) is changing in a frequency band of 22 to 292 GHz. The MEMR spectrum is received from mixer (80) and transmitted through wave guide channel (82) to intermediate frequency amplifier (90), which has a gain of 20 to 25 dB. The intermediate frequency amplifier (90) is controlled by gain and receiving/transmission mode relative to the waveguide channel (92) through channel (66a); amplifier (90) in turn controls the retranslator (20) through wave guide channel (28). Having been processed by the intermediate frequency amplifier (90), the spectrum is next sent to mixer (110) through wave guide channel (92); also to mixer (110) a Heterodyne signal is sent in a frequency band of 22 to 292 Ghz through Heterodyne channel (102). The MEMR spectrum is next transmitted to the multi-channel output commutator(120) through wave guide channel(112). The multi-channel output commutator (120), controlled by signals sent through channel (66d), is connected through wave guide channels (24b) to the transmitting antennas (22b) by which the processed MEMR spectrum is administered to the appropriate BAPs of the target organism. If an MEMR spectrum is received from the target organism's BAPs (30) intermediate frequency amplifier (90), the receiving mode for the mixer (110) is set through channel (66A) working in the same manner as when receiving MEMR spectrum from the control organism's BAPs described above.

The process and apparatus described allow the synthesis and transmission of any number of MEMR spectra, in any desired sequence, with efficiency and precision. In addition to its versatility and controllability, an important positive quality of the invention is its diagnostic capability via the reverse informational connection maintained through channels (12) and (34). These channels supply information about the current state of the control and target organisms, allowing rapid and accurate adjustment of MEMR spectral administration. The aforementioned characteristics result in a superior apparatus for the reception, analysis, generation and administration of MEMR signals to living organisms.

I claim:

1. A process for receiving, analyzing, generating and transmitting microwave spectra comprising:
   (a) receiving a first microwave spectrum from selected biologically active points of a first living organism;
   (b) receiving a second microwave spectrum from selected biologically active points of a second living organism;
   (c) comparing the first and second microwave spectra of the first and second living organisms;
   (d) selecting all spectral characteristics received from the first organism which differ from those spectral characteristics received from the second organism;
   (e) generating a third microwave spectrum identical to that received from the first organism and not received from the second organism;
   (f) transmitting said third microwave spectrum to selected biologically active points of the second organism; and
   (g) continuously monitoring biophysical information from the first and second organisms.

2. The process of claim 1 wherein the microwave spectrum received, analyzed, generated and transmitted has a spectral power density of no more than $10^{-9}$ W/Hz and a frequency band of 30 to 300 GHz.

3. The process of claim 1 wherein the complete microwave spectrum received from the first living organism is transmitted to the second living organism.

4. A process for receiving, analyzing, generating and transmitting microwave spectra comprising:
   (a) receiving a microwave spectrum from selected biologically active points of a living organism;
   (b) comparing the microwave spectral characteristics of the organism to a standardized spectrum from similar organisms;
   (c) selecting all spectral characteristics from the standardized spectrum which differ from those received from the organism;
   (d) generating a third microwave spectrum identical to the spectrum present in the standardized array and absent from the organism;
   (e) transmitting said third microwave spectrum to selected biologically active points of the organism; and
   (f) continuously monitoring biophysical information from said organism during transmission of the generated microwave spectrum.

5. The process of claim 4 wherein all microwave spectra received, analyzed, generated and transmitted have a spectral power density of no more than $10^{-9}$ W/Hz and a frequency band of 30 to 300 GHz.

6. The process of claim 4 wherein the complete standardized microwave spectrum is transmitted to the living organism.

7. An apparatus for receiving, analyzing, generating and transmitting microwave spectra, comprising:
   (a) a receiver for receiving a first microwave spectrum from selected biologically active points of a first living organism;
   (b) a receiver for receiving a second microwave spectrum from selected biologically active points of a second living organism;
   (c) a comparator for comparing the microwave spectral characteristics of said first and second living organisms;
   (d) a selector for selecting the spectral characteristics from the first organism which differ from those received from the second organism;
   (e) a generator for generating a third microwave spectrum identical to the spectrum received from the first organism and not received from the second organism;
   (f) a transmitter for transmitting said third microwave spectrum to selected biologically active points of the second organism;
   (g) a first monitor for continuously monitoring biophysical information from the first organism; and
   (h) a second monitor for continuously monitoring biophysical information from the second organism.

8. The apparatus according to claim 7 wherein a single receiver is employed for serial receipt of microwave spectra from the first and the second living organisms.

* * * * *